US011993711B2

(12) United States Patent
Seifalian et al.

(10) Patent No.: US 11,993,711 B2
(45) Date of Patent: May 28, 2024

(54) COMPOSITE MATERIAL AND ITS METHOD OF PRODUCTION (71) Applicant: NANOREGMED LIMITED, London (GB)

(72) Inventors: Alexander Seifalian, London (GB); Stephen Hancock, London (GB)

(73) Assignee: NANOREGMED LIMITED, London (GB)

(*) Notice: Subject to any disclaimer, the term of this patent is extended or adjusted under 35 U.S.C. 154(b) by 335 days.

(21) Appl. No.: 16/628,098

(22) PCT Filed: Jul. 5, 2018

(86) PCT No.: PCT/GB2018/051918
§ 371 (c)(1),
(2) Date: Jan. 2, 2020

(87) PCT Pub. No.: WO2019/008381
PCT Pub. Date: Jan. 10, 2019

(65) Prior Publication Data
US 2020/0123381 A1 Apr. 23, 2020

(30) Foreign Application Priority Data
Jul. 5, 2017 (GB) .................................. 1710814

(51) Int. Cl.
| C08L 75/06 | (2006.01) |
| A61L 27/44 | (2006.01) |
| A61L 27/50 | (2006.01) |
| A61L 29/12 | (2006.01) |
| C01B 32/15 | (2017.01) |
| C08G 18/10 | (2006.01) |
| C08G 18/44 | (2006.01) |
| C08G 18/48 | (2006.01) |
| C08G 18/76 | (2006.01) |
| C08G 18/83 | (2006.01) |
| C08J 5/00 | (2006.01) |
| C08K 3/04 | (2006.01) |
| C08L 75/00 | (2006.01) |
| C08L 75/02 | (2006.01) |
| C08L 75/04 | (2006.01) |
| C08L 75/08 | (2006.01) |
| C08L 75/10 | (2006.01) |

(52) U.S. Cl.
CPC ............. *C08L 75/06* (2013.01); *A61L 27/443* (2013.01); *A61L 27/507* (2013.01); *A61L 29/126* (2013.01); *C01B 32/15* (2017.08); *C08G 18/10* (2013.01); *C08G 18/44* (2013.01); *C08G 18/4841* (2013.01); *C08G 18/7621* (2013.01); *C08G 18/7671* (2013.01); *C08G 18/831* (2013.01); *C08G 18/833* (2013.01); *C08J 5/005* (2013.01); *C08K 3/04* (2013.01); *C08K 3/041* (2017.05); *C08K 3/042* (2017.05); *C08K 3/043* (2017.05); *C08K 3/044* (2017.05); *C08K 3/045* (2017.05); *C08K 3/046* (2017.05); *C08L 75/00* (2013.01); *C08L 75/02* (2013.01); *C08L 75/04* (2013.01); *C08L 75/08* (2013.01); *C08L 75/10* (2013.01); *A61L 2400/12* (2013.01); *A61L 2430/14* (2013.01); *A61L 2430/20* (2013.01)

(58) Field of Classification Search
CPC .... A61L 27/443; A61L 29/126; A61L 27/507; A61L 2400/12; A61L 2430/14; A61L 2430/20; C08J 5/005; C08K 3/04; C08K 3/043; C08K 3/044; C08K 3/046; C08K 3/042; C08K 3/041; C08K 3/045; C08L 75/06; C08L 75/00; C08L 75/02; C08L 75/04; C08L 75/08; C08L 75/10; C08G 18/10; C08G 18/44; C08G 18/4841; C08G 18/7621; C08G 18/831; C08G 18/833; C01B 32/15
See application file for complete search history.

(56) References Cited

U.S. PATENT DOCUMENTS

| 4,271,217 A * | 6/1981 | Tanaka ...................... D01F 6/70 427/155 |
| 8,318,838 B2 | 11/2012 | Agrawal et al. |
| 10,344,130 B2 | 7/2019 | Sun et al. |
| 10,683,403 B2 | 6/2020 | Sun et al. |
| 2007/0037940 A1* | 2/2007 | Lazzari .................. C08G 61/08 526/171 |
| 2008/0188825 A1 | 8/2008 | Atanasoska et al. |
| 2012/0234204 A1 | 9/2012 | Unal et al. |
| 2013/0101540 A1 | 4/2013 | Unal et al. |

(Continued)

FOREIGN PATENT DOCUMENTS

| CN | 103265685 A | 8/2013 |
| CN | 105693994 A | 6/2016 |

(Continued)

OTHER PUBLICATIONS

Ramirez et al., "Preparation of Urea Functionalized Carbon Nanotubes", Polymer Preprints (ACS, Div. of Polymer Chem.), 2009, 50(1), pp. 453-454.*

(Continued)

*Primary Examiner* — Patrick D Niland
(74) *Attorney, Agent, or Firm* — Oliff PLC (57) ABSTRACT This invention relates to a composite material which is a copolymer of at least (i) a functionalised carbon nanoparticle, (ii) a polyol, (iii) a compound comprising at least two isocyanate groups, wherein the functionalised carbon nanoparticle and the polyol are covalently bonded by a urethane and optionally a urea and/or an amide linkage, and a process for producing the same. Such composite materials are suitable for use in moulded articles for implantation within a mammal.

17 Claims, 5 Drawing Sheets

(56) References Cited

U.S. PATENT DOCUMENTS

| | | | |
|---|---|---|---|
| 2014/0011903 A1 | 1/2014 | Bosnyak et al. | |
| 2014/0275323 A1 | 9/2014 | Thibodeau et al. | |
| 2015/0197641 A1 | 7/2015 | Choi et al. | |

FOREIGN PATENT DOCUMENTS

| | | | |
|---|---|---|---|
| CN | 106632958 A | | 5/2017 |
| EP | 2 868 626 A1 | | 5/2015 |
| EP | 3129422 B1 | | 3/2021 |
| WO | 2005/070988 A1 | | 8/2005 |
| WO | 2005/070998 A1 | | 8/2005 |
| WO | WO 2009/143247 | * | 11/2009 |
| WO | 2014/011527 A1 | | 1/2014 |
| WO | 2014/143758 A2 | | 9/2014 |
| WO | WO 2015/160764 | * | 10/2015 |
| WO | 2016/078664 A1 | | 5/2016 |

OTHER PUBLICATIONS

Oct. 2, 2018 International Search Report issued in International Patent Application No. PCT/GB2018/051918.

Oct. 2, 2018 Written Opinion of the International Searching Authority issued in International Patent Application No. PCT/GB2018/051918.

Dec. 29, 2017 Search Report issued in British Patent Application No. 1710814.3.

Jan. 8, 2019 Search and Examination Report issued in British Patent Application No. 1811090.8.

Cai, Dongyu, "High performance polyurethane/functionalized graphene nanocomposites with improved mechanical and thermal properties," Composites Science and Technology, 2012, vol. 72, pp. 702-707.

Patel, Dinesh K., et al., "Superior Biomaterials Using Diamine Modified Graphene Grafted Polyurethane," Polymer, 2016, vol. 106, pp. 109-119.

Depan, D. et al., "Structure-process-property relationship of the polar graphene oxide-mediated cellular response and stimulated growth of osteoblasts on hybrid chitosan network structure nanocomposite scaffolds," Acta Biomaterialia, vol. 7, pp. 3432-3445, 2011.

Ahadian, S. et al., "Electically regulated differentiation of skeletal muscle cells on ultrathin graphene-based films," Royal Society of Chemistry, vol. 4, pp. 9534-9541, 2014.

Nezakati, T., "Development of a Graphene-POSS-Nanocomposite Conductive Material for Biomedical Application," PhD Thesis, University College London, Mar. 2015.

Naderi et al., "Adipogenic differentiation of adipose-derived stem cells in 3-dimensional spheroid cultures (microtissue): implications for the reconstructive surgeon," Journal of Plastic, Reconstructive & Aesthetic Surgery, (2014), 67(12), 1726-1734.

Gholipourmalekabadi et al., "Decellularized human amniotic membrane: how viable is it as a delivery system for human adipose tissue-derived stromal cells?," Cell Proliferation, (2016), 49(1), 115-121.

Griffin et al., "Chemical group-dependent plasma polymerisation preferentially directs adipose stem cell differentiation towards osteogenic or chondrogenic lineages," Acta Biomaterialia, (2017), 50, 450-461.

Rago et al., "DNA fluorometric assay in 96-well tissue culture plates using Hoechst 33258 after cell lysis by freezing in distilled water," Analytical Biochemistry, (1990), 191(1), 31-34.

Textbook p. 753, ODIAN, "Principles of Polymerization," 4th Edition, 2016 reprint, Wiley; ISBN, 978-81-2651391-8.

* cited by examiner

COMPOSITE MATERIAL AND ITS METHOD OF PRODUCTION

This application is a U.S. national stage filing under 35 U.S.C. § 371 of International Application No. PCT/GB2018/051918, filed on Jul. 5, 2018, which claims the benefit of priority to GB Application No. 1710814.3, filed on Jul. 5, 2017.

This invention relates to a composite material which is a copolymer of at least (i) a functionalised carbon nanoparticle, (ii) a polyol, (iii) a compound comprising at least two isocyanate groups, wherein the functionalised carbon nanoparticle and the polyol are covalently bonded by a urethane and optionally a urea and/or an amide linkage, and a process for producing the same. Such composite materials are suitable for use in moulded articles for implantation within a mammal.

The availability of biomaterial scaffolds, which can be used to regenerate or replace irreversibly damaged organs, is a significant unmet need in the niche of regenerative medicine. Specific examples include facial organs such as the nose or the ear damaged by cancer, trauma or congenital deformity. At present, reconstruction involves taking cartilage from the ribs and is invasive and the outcome is not effective because cartilage does not mimic well the viscoelastic properties of the nose or ear.

Other body parts which often need replacement include calcified heart valve leaflets. At present, replacement mechanical heart valves are used but they suffer from thrombogenicity, durability, rejection and calcification. Another example is for heart by-pass surgery which, at present, requires transfer of vascular tissue from another part of the body to around the heart. Synthetic vascular graft materials suffer from lack of biocompatibility and thrombosis.

Another medical application with an unmet need is the urinary catheter where patients often suffer from infection and irritation.

WO 2005/070998 (UCL Biomedica Plc) discloses a copolymer comprising (a) one or more polysiloxane-containing segments and (b) one or more polyol segments, each of said segments being linked to one or more further segments, which may be the same or different, via urea or urethane linkages, wherein said polysiloxane-containing segment(s) are in the backbone of the copolymer. The copolymer is useful in the production of implantable devices such as vascular grafts.

WO 2005/070988 (UCL Biomedica Plc) discloses a copolymer comprising (a) one or more pendant group segments and (b) one or more polyol segments, each of said segments being linked to one or more further segments, and one or more of the pendant group segments being selected from: (i) siloxane segments; (ii) segments containing phosphoryl choline or a derivative or analogue thereof; (iii) segments containing a di- or trifluoromethyl group; (iv) heparin-like segments containing a group of formula: (XII) D-N=N—Ar—$SO_3^-$ (v) segments containing a group of formula: (I) $[P]_{n'}$-$[Lys]_n$-Lys-[Spacer]-Lys-$[Al]_x$ in which D, Ar, P, Lys, Al, Spacer, x, n and n' are as defined herein, and wherein at least a part of each of said pendant group segment(s) is on a side chain of the copolymer. The copolymer is useful in the production of implantable devices such as vascular grafts.

The copolymers described in WO 2005/070998 (UCL Biomedica Plc) and WO 2005/070988 (UCL Biomedica Plc) have shown a lack of integration with the surrounding tissue.

BRIEF DESCRIPTION OF THE INVENTION

In a first aspect of the invention, a process for producing a composite material comprising a first segment covalently bonded to a second segment by a urethane and optionally a urea and/or an amide linkage, wherein the first segment is a carbon nanoparticle moiety and the second segment is a polyol moiety is provided, the process comprising a first step of polymerising (i) a functionalised carbon nanoparticle, (ii) a polyol, (iii) a compound comprising at least two isocyanate groups, and optionally (iv) a chain extending compound comprising at least two chemical groups selected from the group consisting of a primary amine, an hydroxyl and a carboxylic group.

In a second aspect of the invention, a composite material is provided, which is a copolymer of (i) a functionalised carbon nanoparticle, (ii) a polyol, (iii) a compound comprising at least two isocyanate groups, optionally (iv) a chain extending compound comprising at least two chemical groups selected from the group consisting of a primary amine, an hydroxyl and a carboxylic group, and optionally (v) a monoamine, wherein the functionalised carbon nanoparticle and the polyol are covalently bonded by a urethane and optionally a urea and/or an amide linkage.

In a third aspect of the invention, a composite material is provided, the composite material obtained or obtainable from the process according to the first aspect of the invention.

In a fourth aspect of the invention, a moulded article is provided, the moulded article comprising the composite material of the second and third aspects of the invention, preferably wherein the moulded article is a device implantable within a mammal, preferably a human being, preferably wherein the device implantable within a mammal is selected from the group consisting of a vascular graft, a replacement ear scaffold or part thereof, a replacement nose scaffold or part thereof, a heart valve leaflet replacement, an urinary catheter, and a neural interface.

BRIEF DESCRIPTION OF THE FIGURES

The invention is illustrated with reference to the figures which show in.

DETAILED DESCRIPTION OF THE INVENTION

In a first aspect of the invention, a process for producing a composite material comprising a first segment covalently bonded to a second segment by a urethane and optionally a urea and/or an amide linkage, wherein the first segment is a carbon nanoparticle moiety and the second segment is a polyol moiety is provided, the process comprising a first step of polymerising (i) a functionalised carbon nanoparticle, (ii) a polyol, (iii) a compound comprising at least two isocyanate groups, and optionally (iv) a chain extending compound comprising at least two chemical groups selected from the group consisting of a primary amine, an hydroxyl and a carboxylic group.

The term "functionalised" means functionalised with any one of carboxylic acid, tertiary alcoholic, epoxide, primary alcoholic or primary amino groups, preferably "functionalised" means functionalised with primary alcoholic or primary amino groups, more preferably where the carbon nanoparticle is graphene, primary alcoholic or primary amino groups are in the plane and on the edge of the graphene sheets. Primary alcohols are more reactive with isocyanate groups than secondary or tertiary alcohols. Graphene oxide comprises carboxylic acid, tertiary alcoholic, epoxide, primary alcoholic or primary amino groups. The carboxylic acid groups can be found on the edge of the graphene sheets in the plane of the sheets.

Preferably the compound comprising at least two isocyanate groups is added to a solution of (i) in (ii) and (i), (ii) and (ii) polymerised, and optionally (iv) subsequently added, or wherein (ii) and (iii) are polymerised thereby to form a pre-polymer, (i) is then polymerised with the pre-polymer and, and optionally (iv) subsequently added.

In a second aspect of the invention, a composite material is provided, which is a copolymer of (i) a functionalised carbon nanoparticle, (ii) a polyol, (iii) a compound comprising at least two isocyanate groups, optionally (iv) a chain extending compound comprising at least two chemical groups selected from the group consisting of a primary amine, an hydroxyl and a carboxylic group, and optionally (v) a monoamine, wherein the functionalised carbon nanoparticle and the polyol are covalently bonded by a urethane and optionally a urea and/or an amide linkage.

Preferably the functionalised carbon nanoparticle is selected from the group consisting of graphene oxide, carbon nanotubes, functionalised graphene oxide, functionalised carbon nanotubes, functionalised fullerene, functionalised graphite, functionalised graphene, functionalised diamond, and functionalised carbon dots, preferably the functionalised carbon nanoparticle is selected from the group consisting of functionalised graphene oxide, functionalised $C_{60}$ fullerene and functionalised carbon nanotubes.

Preferably the polyol is selected from the group consisting of a polycarbonate polyol, a polycaprolactone diol (for example UBE Eternacoll PH-200 (average molecular weight of about 2000), Sigma Aldrich polycapralactone diol (number average molecular weight 2000) and Perstorp Oxymer M112 (molecular weight 1000)), a polyether polyol (for example, Invista Terethane PTMEG 2000 (molecular weight 1900-2100)), a polyester polyol, a polybutadiene polyol (for example, Cray Valley Krasol LBH 2000 (number average molecular weight 2100)), a polyol comprising pendant polyethylene oxide, and mixtures thereof, preferably the polyol is a polycarbonate polyol or a polyether polyol.

Polycarbonate polyol is non-biodegradable and is hence more biocompatible due to a decreased rate of oxidation and hydrolysis in-vivo, and can be used as a scaffold for arterial bypass grafts or heart valve leaflet implants. Other useful properties are its viscoelastic properties and crack resistance.

Polyether polyol has useful non-medical applications such as in anti-biofouling applications for the marine environment.

Preferably the compound comprising at least two isocyanate groups is an aliphatic or aromatic compound, preferably the compound comprising at least two isocyanate groups is an aromatic compound. Aromatic compounds are preferred because they bond more strongly to graphene nanoparticles due to pi stacking overlap with graphene nanoparticles. This effect would also be expected with graphene and graphite. Furthermore aromatic compounds also have better mechanical properties. Preferably the compound comprising at least two isocyanate groups comprises two or three or four or five or six isocyanate groups.

In one embodiment, the compound comprising at least two isocyanate groups is selected from the group consisting of toluene 2,4-diisocyanate, 1,3-bis(1-isocyanato-1-methylethyl)benzene, and methylenebisphenyl isocyanate (both the 2,4- and 4,4'-isomers), preferably the compound comprising at least two isocyanate groups is methylenebisphenyl isocyanate.

Preferably, the chain extending compound comprising at least two chemical groups, comprises two or three chemical groups. Preferably, the chain extending compound comprises identical or non-identical chemical groups. In one embodiment, the chain extending compound is selected from the group consisting of an aliphatic amine, an aliphatic carboxylic acid, an aliphatic alcohol, a functionalised silica nanoparticle, an amino acid, a peptide, and a polypeptide, preferably the peptide is RGD. The term "functionalised" has been previously defined. RGD is arginylglycylaspartic acid and is a tripeptide composed of L-arginine, glycine, and L-aspartic acid. RGD is a non-thromogenetic, anti-coagulant which enhances endothelialisation in cardiovascular applications where, for example, the inner surface of a tubular scaffold is seeded with endothelial cells.

Preferably, the second segments are of the same or different polyols, preferably the second segments are of the same polyol. Preferably, the second segments are of the same or different number average molecular weights, preferably the second segments are of different number average molecular weights. Preferably the second segment has a number average molecular weight of 1-4 kD. Preferably, the weight ratio of first segments to second segments is at least 1:50, preferably at least 1:30, most preferably at least 1:20. An excess of first segments provides a composite material which is very compatible with blood but with a lower ability to grow cells on its surface, thus the claimed ratio of first and second segments provides a composite material which still possesses good blood compatibility and with adequate ability for cells to grow on its surface. Even more preferably the weight ratio is at least 1:15, or at least 1:10.

Preferably the process of the first aspect of the invention comprises a second step of adding a monoamine after completion of the first step. This chain termination step also makes the composite material more electronegative and easier to disperse in water.

In a third aspect of the invention, a composite material is provided, the composite material obtained or obtainable from the process according to the first aspect of the invention.

In a fourth aspect of the invention, a moulded article is provided, the moulded article comprising the composite material of the second and third aspects of the invention, preferably wherein the moulded article is a device implantable within a mammal, preferably a human being, preferably wherein the device implantable within a mammal is selected from the group consisting of a vascular graft, a replacement ear scaffold or part thereof, a replacement nose scaffold or part thereof, a heart valve leaflet replacement, and an urinary catheter.

Moulded articles are prepared using methods known in the art for preparing thermoplastic articles.

EXAMPLES

Nanocomposite Copolymer Thin Film Fabrication

Nanocomposite copolymer solutions were cast into 10 cm by 10 cm sheets at a dry film thickness of 100 μm by applying the solutions onto glass panels using a 100 micron bar film applicator. The panels were then placed in an air circulating oven at 65° C. for a minimum of 16 hours. It was noted that the surface of the film facing the glass was shiny whilst the opposite surface was matt.

Nanocomposite Copolymer Solution: Viscosity and Density

Nanocomposite copolymer solutions were allowed to stabilise for two days after synthesis prior to measurement of their viscosities and densities at 25° C. Viscosities were measures on a rotary viscometer (J.P Selecta, Spain) in accordance with ISO standard 2555:1989 (Plastics—Resins in the liquid state or as emulsions or dispersions—Determination of apparent viscosity by the Brookfield Test method). Densities were measured in accordance with ISO standard 1183-1:2012 (Plastics—Methods for determining the density of non-cellular plastics—Part 1: Immersion method, liquid pyknometer method and titration method). The density was determined using a standard 25 ml density bottle (VWR, Lutterworth, UK) and calibration carried out by determining the density of deionised water and ethanol.

Nanocomposite Copolymer Thin Film: Mechanical Properties

Nanocomposite copolymer thin films were conditioned at 23° C. and 50% relative humidity for a minimum of 16 hours. The tensile strength of the films was measured on an Instron 5565 tensile and compression tester equipped with a 500 N load cell at a crosshead speed of 500 mm/min with dumb bell shaped specimen (size type 3: 20 mm shaft length, 4 mm width) in accordance with ISO standard 37:2011 (Rubber, vulcanized or thermoplastic—Determination of tensile stress-strain properties). The thin film thickness was measured using a micrometer. Five replicate samples were tested (n=5). The Young's Modulus was calculated from the slope of the stress-strain curves in the range 0-300% elongation.

A suture retention strength test was also carried out on the films. Films were cut into 5 mm×20 mm test samples and a loop of 3-0 nylon suture sutured 2 mm from one end. The other end of the test samples was clamped and loaded until failure under the same test conditions as for the tensile strength test.

Nanocomposite Copolymer Thin Film: Surface Morphology

Evaluation of the surface morphology of both sides of the nanocomposite copolymer thin films was assessed using scanning electron microscopy (Philips XL30, Netherlands). Test samples were prepared by sputter coating them using a gold target.

The height distribution and roughness of both sides of the nanocomposite copolymer thin films were also imaged and quantified using atomic force microscopy (DME, Germany).

Nanocomposite Copolymer Thin Film: Contact Angle

Static water contact angle measurements, which is a measure of the hydrophobicity of the test surface, were performed using a Krüss system in accordance with the sessile drop method. A 20 microlitres water droplet was placed onto the surface of the films and the angle between water droplet-horizon was measured. The test was repeated five times.

Nanocomposite Copolymer Thin Film: In-Vitro Biocompatibility

The behaviour of human adipose tissue-derived stem cells (ADSCs) and human fibroblasts after exposure to nanocomposite copolymer thin films was determined in-vitro.

ADSCs were isolated from human adipose tissue in accordance with Naderi et al. (J. Plast. Reconstr. Aesthet. Surg. 67, 12, 1726 (2014)), Gholipourmalekabadi et al. (Cell Prolif., 49, 1, 115 (2016)), and Griffin et al. (Acta Biomater., 1, 50, 450 (2017)). In brief, adipose tissue was collected from patients undergoing liposuction surgery after informed consent and transferred in normal saline (0.90% w/v NaCl) under sterile conditions. The tissue was then treated with 0.2% w/v collagenase II (Sigma, USA) for 30 minutes at 37° C. to lyse the extracellular matrix. The tissue was then centrifuged and the supernatant discarded. The resultant pellet was seeded in a cell culture flask containing supplemented Dulbecco's Modified Eagle Medium low glucose (DMEM supplemented with 10% w/v fetal bovine serum and 1% w/v pen/strep (100 U/ml penicillin and 100 micrograms/ml streptomycin)) and incubated at 95% relative humidity with 5% $CO_2$ at 37° C. until reaching 90% confluence. The cells obtained from the second passage were used.

Adult primary fibroblasts from human dermis was purchased and cultured in Dulbecco's Modified Eagle Medium (DMEM) supplemented with 1 mM L-glutamine, 1% w/w penicillin/streptomycin, 10% w/w fetal bovine serum (FBS) and 1% w/w Fungizone (amphotericin B). Fibroblasts were cultured to 80-90% confluency, trypsinized (Sigma, USA). The cells collected from second passage were used in this study.

The cell viability of both the ADSCs and human fibroblasts in the presence of the nanocomposite copolymer thin film was determined using the MTT (3-(4,5-dimethylthiazol-2-yl)) assay. This assay is a colourimetric assay for assessing cell metabolic activity and is based on the reduction of the tetrazolium dye MTT by NAD(P)H-dependent cellular oxidoreductase enzymes to its insoluble formazan which is purple in colour. The level of NAD(P)H-dependent cellular oxidoreductase enzyme activity is a measure of the number of viable cells. In accordance with the instructions on the MTT assay kit (Sigma), $2\times10^3$ cells were seeded on the films and incubated at 37° C. for 1, 2, 3, 4, 7, 10, 14 and 21 days after which the cells were treated with 10% w/v MTT solution in supplemented DMEM for 1 hour at 37° C. The cells were then treated with dimethyl sulfoxide and stored in a dark chamber for 15 minutes. The optical density was measured using an ELISA microplate reader at a wavelength of 590 nm. The cells cultured on the plastic surface of a culture plate served as a control and their viability was considered as 100%.

Cell apoptosis and necrosis of both the ADSCs and human fibroblasts in the presence of the nanocomposite copolymer thin film was determined using flow cytometry after staining with Annexin V ApopNexin FITC (fluorescein isothiocyanate) Apoptosis Detection Kit in combination with propidium iodide (a fluorescent intercalating agent that can be used to stain cells) (Merck, USA). The kit contains Annexin V conjugated to FITC and the counter-stain propidium iodide. Annexin V, a member of a family of proteins that bind specifically to cellular membranes, has a particular affinity to membranes containing the negatively charged phospholipid phosphatidylserine. Phosphatidylserine is normally confined to the inner membrane leaflet of viable cell, but in early apoptosis, is translocated to the exposed membrane surface. In contrast in cell necrosis, the cell membrane becomes permeable allowing the hydrophilic dye propidium iodide to stain the nucleus. However cells in the early stages of apoptosis do not have permeable membranes. $4\times10^5$ cells were cultured on the nanocomposite copolymer thin films in accordance with the kit instructions and the assay performed. The percentages of necrotic and apoptotic cells were then measured using flow cytometry. The cells cultured on the plastic surface of a culture plate served as a control.

Cell adhesion of both the ADSCs and human fibroblasts grown on both the shiny and matt sides of the nanocomposite copolymer thin films was investigated using scanning electron microscopy. Cells were seeded on the films for 24 hours in a standard cell culture incubator. The cells were then fixed with 2.5% w/v glutaraldehyde and stained with 0.1% w/v osmium tetroxide for 30 minutes. The samples were then dehydrated through a graded ethanol series and freeze dried, coated with gold by sputter coating and the morphology of the cells viewed under a scanning electron microscope.

The density of both the ADSCs and human fibroblasts grown on both the shiny and matt sides of the nanocomposite copolymer thin films was investigated by staining the cells with 4',6-diamidine-2-phenylindole (DAPI) and counting of the average number of the cells in ten high-power fields using a fluorescence microscope. The cells cultured on the plastic surface of a culture plate served as a control.

Nanocomposite Copolymer Thin Film: Preclinical Model In-Vivo Biocompatibility

Nanocomposite copolymer thin films were autoclaved prior to being placed subcutaneously into the back of normal, healthy BALB/c mice model (n=5). Surgery without implantation of a film served as a control. After 3 and 7 days, the film implants were removed from experimental animal groups and surrounding tissue removed from both experimental and control animal groups. The tissue was then kept in 10% w/v formalin for histopathological examination using haematoxylin-eosin stain. The average numbers of inflammatory cells infiltrated into the implanted site were in ten high-power fields were counted.

Example 1: Synthesis of Graphene Oxide Functionalised with Amine Groups 3 g of graphene oxide (Sigma) (graphene oxide comprises epoxide, hydroxyl and carboxylic acid groups and it was the carboxylic acid groups which are most relevant in this example) was dispersed in toluene using ultrasonication for 30 minutes, cooled to 4° C., and 3 mL concentrated sulfuric acid added drop-wise and the mixture continuously stirred for 40 minutes. Then 3 g of sodium azide was added to the mixture gradually for 30 minutes while continuously stirring. The mixture was then stirred for a period of 12 hours at 60° C., cooled down, diluted with distilled water, filtered and dried under vacuum at 65° C. for 12 hours thereby to produce an intermediate product. 2 g amine of the intermediate product was then dispersed in N,N'-dimethylformamide (DMF) and reduced with 50 mL hydrazine at 70° C. for 12 hours, filtered, washed with deionized water, and dried under vacuum at 65° C. for 10 hours thereby to produce amine functionalised graphene oxide.

Example 2: Synthesis of a Functionalised Graphene Oxide-Polycarbonate Copolymer 5 g amine functionalised graphene oxide of Example 1 and 55 g 2000 MW polycarbonate polyol (Sigma) were added to a 500 ml flask containing a mechanical stirrer and nitrogen inlet. The mixture was heated to 80° C. at which point the functionalised graphene oxide dissolved in the polycarbonate polyol. The mixture was then cooled to 40° C., at which point 16 g 4,4'-methylenebisphenyl isocyanate (MDI) was added to the mixture and the temperature maintained at 75 to 85° C. for 90 minutes thereby to form a pre-polymer. 300 g of dimethylacetamide or dimethyl sulfoxide (DMSO) was then added to the pre-polymer over one hour allowing the temperature to cool to 40° C. thereby to form a pre-polymer solution. A mixture of ethylenediamine and diethylamine in the weight ratio of 7.6:1 as a 3.3% w/v dimethylacetamide solution was then added drop-wise to the pre-polymer solution at 40° C. over one hour thereby to create a solution of functionalised graphene oxide-polycarbonate copolymer comprising urea and urethane linkages in dimethylacetamide or DMSO. 3 g of 10% w/v butanol in dimethylacetamide was then added to the solution of functionalised graphene oxide-polycarbonate copolymer to neutralise any excess isocyanate thereby to produce a neutralised functionalised graphene oxide-polycarbonate copolymer solution.

The final solids content was 20% w/w. The viscosity of the neutralised functionalised graphene oxide-polycarbonate copolymer solution was 3850+/−96 mPas. The density of the neutralised functionalised graphene oxide-polycarbonate copolymer solution was 1.186+/−0.010 g/ml.

Example 3: Physical Properties of Thin Films of the Functionalised Graphene Oxide-Polycarbonate Copolymer of Example 2

Thin films (100 micron thickness) were prepared as previously described and measured at five locations using a micrometer. Tests were repeated six times. The maximum load for the tensile strength test was 63.5+/−2.6 MPa. The % elongation for the tensile strength test was 898.1+/−21.3%. The Young's Modulus for the tensile strength test was 26.7+/−1.5 MPa. The tear strength of the thin film was 64.63+/−2.1 MPa. The stress at suture break was 6.5+/−0.5 MPa.

Figure 1:
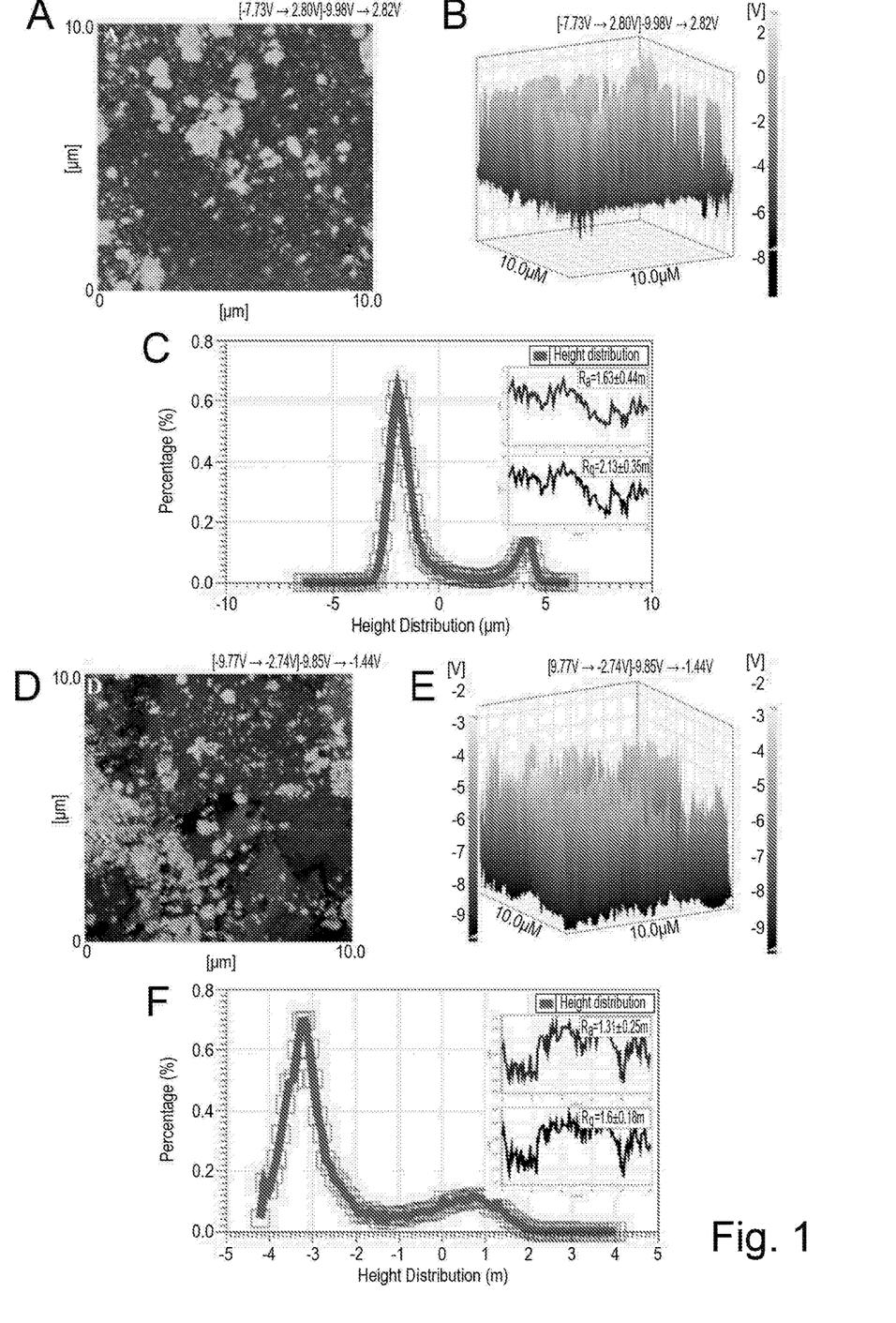
FIG. 1 the height distribution profile and roughness of both surfaces of the thin film of the functionalised graphene oxide-polycarbonate copolymer of Example 2, wherein "A" and "D" are the atomic force 2D micrographs of the shiny and matt surfaces respectively; "B" and "E" are the corresponding 3D images; and "C" and "F" are the height distribution profiles, Ra and Rq (surface roughness measurements) of the shiny and matt surfaces respectively.

FIG. 1 illustrates the average height distribution profile, Rq (root-mean-squared roughness) and Ra (average roughness), of both surfaces of the thin film of the functionalised graphene oxide-polycarbonate copolymer of Example 2 calculated using Gwyddion software, as well as 2D and 3D atomic force micrographs of both surfaces. The average height of shiny and matt surfaces was −61.1 nm and −2.26 nm respectively. The Rq values were 9.4±15.3 nm and 400±270 nm for the shiny and matt surfaces respectively. The Ra values were 4.1±4.4 nm and 220±140 nm for the shiny and matt surfaces respectively. According to these results, the average height distribution and roughness of the shiny surface were lower than those of the matt side.

The mean contact angles for the shiny and matt surfaces were 68.87±1.55 degrees and 85.10±2.27 degrees respectively (n=6). It is surmised that as graphene has a naturally strong self-assembling behaviour, to minimise the overall surface free energy of the functionalised graphene oxide-polycarbonate copolymer of Example 2, the shiny and matt surfaces are dominated by the functionalised graphene oxide moiety rather than the polycarbonate moiety, hence the high contact angles. A high contact angle is useful in medical applications as it is harder for bacteria to gain a purchase of high energy surfaces and therefore the incidence of infection is reduced. On the other hand, a surface energy which is too high is less biocompatible because the rate of cellular proliferation is reduced. It can also be expected that tubes of functionalised graphene oxide-polycarbonate copolymer of Example 2 will exhibit more resistance to degradation compared to polycarbonate-urethane whilst retaining radial elasticity.

Example 4: In-Vitro and In-Vivo Biocompatibility of Thin Films of the Functionalised Graphene Oxide-Polycarbonate Copolymer of Example 2

Figure 2:
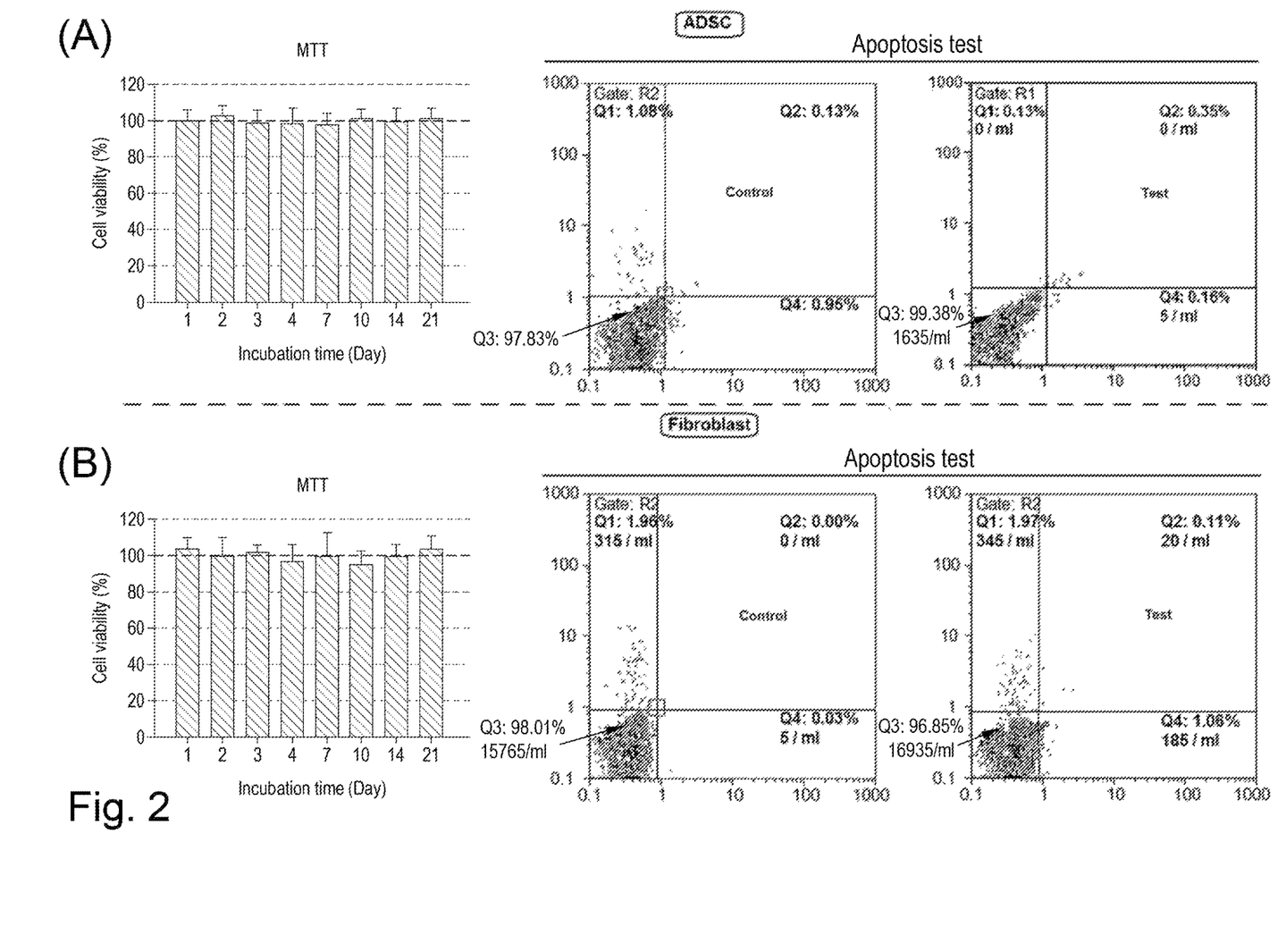
FIG. 2 the viability of human adipose tissue-derived stem cells (ADSCs) ("A") and human fibroblasts ("B") on thin films of the functionalised graphene oxide-polycarbonate copolymer of Example 2 as measured using an MTT based assay after incubation for 1, 2, 3, 4, 7, 10, 14 and 21 days, the degree of apoptosis ("Q4") of ADSCs ("A") and human fibroblasts ("B") on thin films of the functionalised graphene oxide-polycarbonate copolymer of Example 2 ("test") and the plastic surface of the culture plate ("control")

FIG. 2 shows that viability of ADSCs ("A") and human fibroblasts ("B") was not affected on thin films (matt surface) of the functionalised graphene oxide-polycarbonate copolymer of Example 2 because the % cell viability, as measured using the MTT based assay described above, remained unchanged after incubation for 1, 2, 3, 4, 7, 10, 14 and 21 days.

FIG. 2 also shows that the degree of apoptosis of ADSCs ("A") and human fibroblasts ("B") was not affected on thin films (matt surface) of the functionalised graphene oxide-polycarbonate copolymer of Example 2 ("test") because there was no significant difference between apoptosis of the cells when cultured on the thin films and the plastic surface of the culture plate. In particular, the average percentage values (n=6) of ADSCs that were under apoptosis on the thin film ("test") and on the plastic surface of a culture plate ("control") were 0.14+/−0.03% and 0.85+/−0.11% respectively ("Q4"). The average percentage values (n=6) of human fibroblasts that were under apoptosis on the thin film ("test") and on the plastic surface of a culture plate ("control") were 0.86+/−0.10% and 0.056+/−0.09% respectively ("Q4").

Figure 3:
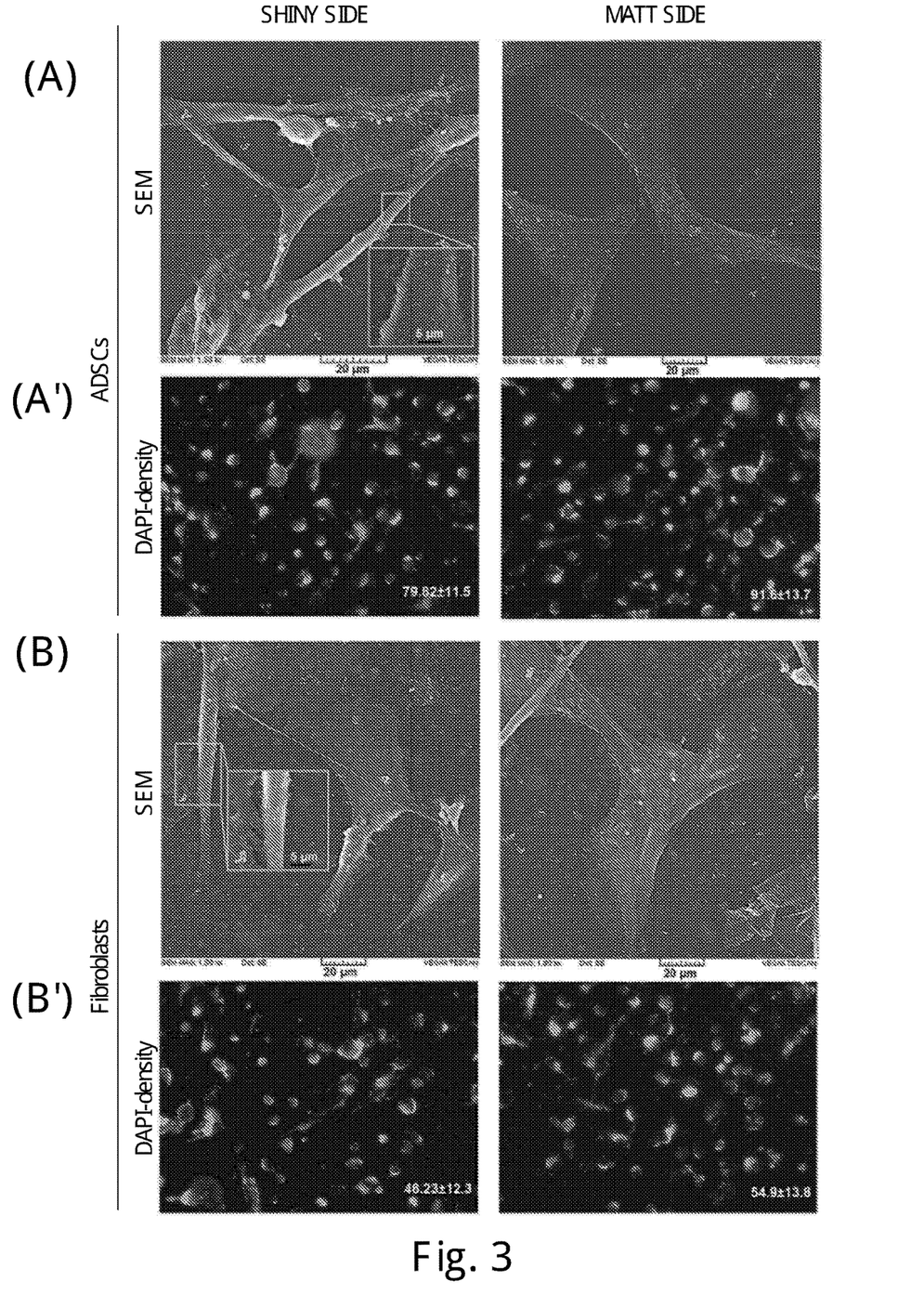
FIG. 3 scanning electron micrographs of ADSCs ("A") and human fibroblasts ("B") seeded on both the shiny and matt surfaces of the thin films of the functionalised graphene oxide-polycarbonate copolymer of Example 2, and fluorescence micrographs of DAPI stained ADSCs ("A'") and human fibroblasts ("B'") seeded on both the shiny and matt surfaces of the thin films of the functionalised graphene oxide-polycarbonate copolymer of Example 2.

FIG. 3 shows scanning electron micrographs of ADSCs ("A") and human fibroblasts ("B") seeded on both the shiny and matt surfaces of the thin films of the functionalised graphene oxide-polycarbonate copolymer of Example 2. The micrographs confirmed the presence of the distinctive stretched (spindle-like) morphology of the ADSCs on both the shiny and matt surfaces of the functionalised graphene oxide-polycarbonate copolymer thin film. Therefore, ADSCs, which are the preferred choice of stem cells because they are easily available pre- or during surgery from patients using liposuction or from surgery, have been shown to adhere to (and preferably proliferate and differentiate on) both the shiny and matt surfaces of the thin films. The micrographs illustrate a good percentage of cell coverage after 24 hours on both surfaces, however there were more cells on the matt surface compared to the shiny surface. This is thought to be due to the higher roughness of the matt surface over the shiny surface.

FIG. 3 also shows fluorescence micrographs of DAPI stained ADSCs ("A'") and human fibroblasts ("B'") seeded on both the shiny and matt surfaces of the thin films of the functionalised graphene oxide-polycarbonate copolymer of Example 2. The average number (n=10) of ADSCs attached to the shiny and matt surfaces of the thin film were 79.8±11.5 and 91.6±13.7 respectively. The average number (n=10) of human fibroblasts attached to the shiny and matt surfaces of the thin film were 48.2±12.3 and 54.9±13.8 respectively. This shows that whilst both surfaces of the thin film are suitable substrates for culturing ADSCs and human fibroblasts, the performance of the matt surface was consistently superior to that of the shiny surface, most probably due to the higher roughness of the matt surface over that of the shiny surface. Also as Depan et al. (Acta Biomater., 7, 3432 (2011)), Ahadian et al. (RSC Adv., 4, 9534 (2014)) and Nezakati (PhD Thesis, University College London (2015)), disclose, graphene provides a surface which enhances cell proliferation and adhesion due to the orientation of graphene agglomerates providing a charged hydrophobic surface, it would then be expected that both the shiny and matt surfaces are dominated by the functionalised graphene oxide moiety rather than the polycarbonate moiety. It was also be expected that thromboresistance would be improved through reduced platelet adhesion due to the minimising of the interfacial energy between blood and the copolymer surface.

Figure 4:
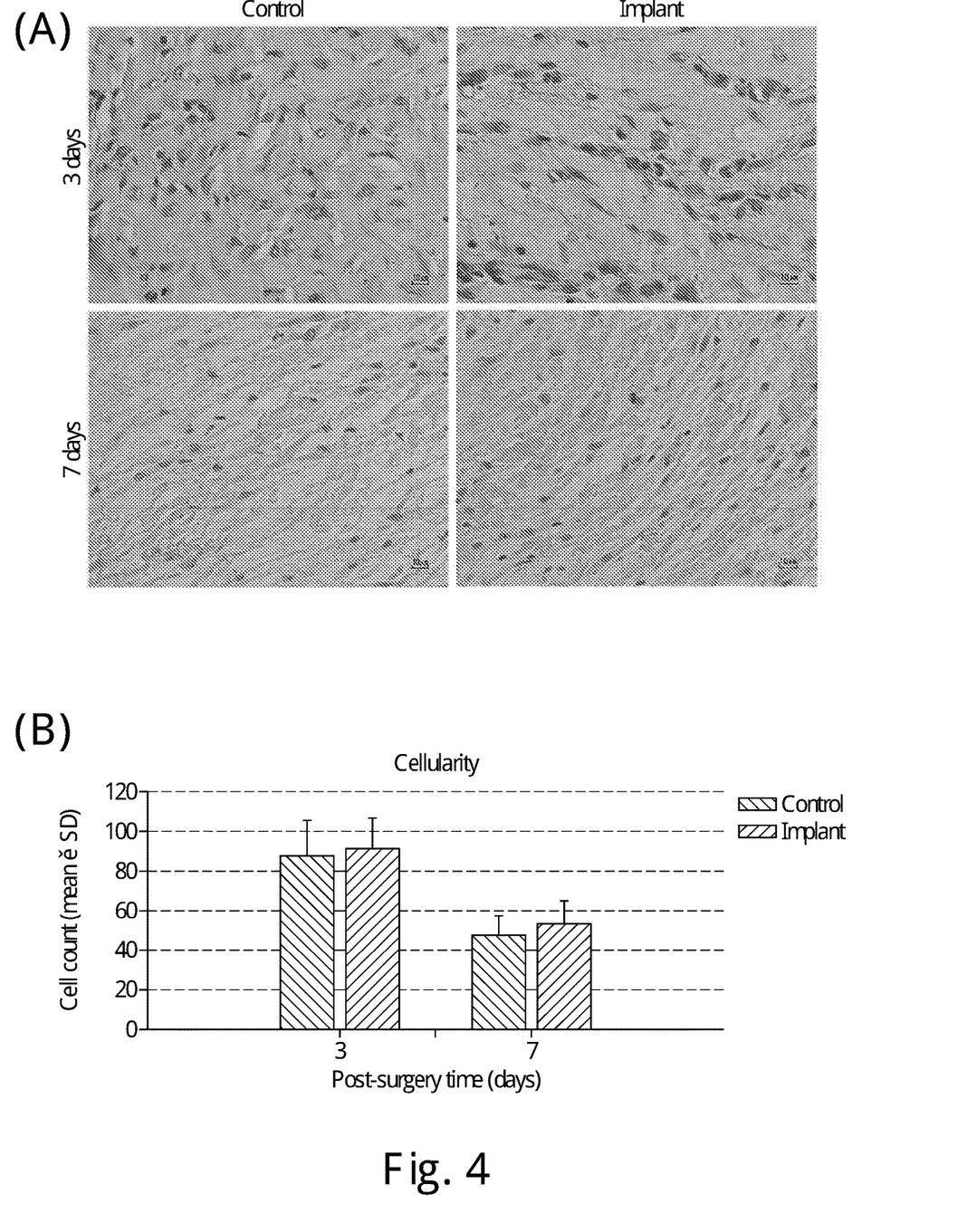
FIG. 4 exemplar micrographs (n=10) ("A") of haematoxylin-eosin stained tissue taken from the back of normal, healthy BALB/c mice model 3 and 7 days after implanting thin films of the functionalised graphene oxide-polycarbonate copolymer of Example 2 ("implant") and after the same surgery but without an implant ("control") showing that no significant inflammatory cells were observed in the implanted area when compared with the control group, and that there was no significant difference between the average number of cells counted infiltrated into the implanted site when compared to the control ("B")

FIG. 4 shows micrographs ("A") of haematoxylin-eosin stained tissue taken from the back of normal, healthy BALB/c mice model 3 and 7 days after implanting thin films of the functionalised graphene oxide-polycarbonate copolymer of Example 2 ("implant") and after the same surgery but without an implant ("control"). FIG. 4 also shows the average number (n=10) of inflammation cells infiltrated into the implant sites ("B") from which it is apparent that there was no significant difference between the average number of the inflammatory cells infiltrated into the implanted site at 3 and 7 days post-implantation when compared with the control. Thus the functionalised graphene oxide-polycarbonate copolymer of Example 2 appears from this test not to provoke an inflammatory response.

Example 5: Synthesis of Carbon Nanotubes and $C_{60}$ Fullerene Functionalised with Amine Groups Synthesis of amine functionalised carbon nanotubes and amine functionalised $C_{60}$ fullerene was carried out in the manner described in Example 1. The non-functionalised carbon nanotubes and non-functionalised $C_{60}$ fullerene were obtained from Sigma.

Example 6: Synthesis of Functionalised Carbon Nanotubes-Polycarbonate Copolymers and Functionalised $C_{60}$ Fullerene-Polycarbonate Copolymers Synthesis of functionalised carbon-based nanoparticles-polycarbonate copolymers based on the amine functionalised carbon nanotubes and amine functionalised $C_{60}$ fullerene of Example 5 was carried out in the manner described in Example 2.

The final solids content of each solution was 20% w/w. The viscosity of the neutralised functionalised carbon nanotubes-polycarbonate copolymer solution was 3721+/−101 mPas. The viscosity of the neutralised functionalised $C_{60}$ fullerene-polycarbonate copolymer solution was 3655+/−98 mPas.

Example 7: Physical Properties of Thin Films of the Functionalised Carbon Nanotubes-Polycarbonate Copolymer and Functionalised $C_{60}$ Fullerene-Polycarbonate Copolymer of Example 6

Thin films (100 micron thickness) were prepared as previously described and measured at five locations using a micrometer. Tests were repeated six times. The maximum loads for the tensile strength test for the functionalised carbon nanotubes-polycarbonate copolymer and the functionalised $C_{60}$ fullerene-polycarbonate copolymer of Example 6 were 65.3+/−5.5 and 61.0+/−4.9 MPa respectively. The % elongation for the tensile strength test for the functionalised carbon nanotubes-polycarbonate copolymer and the functionalised $C_{60}$ fullerene-polycarbonate copolymer of Example 6 were 702.1+/−32.0 and 733.9+/−46.2% respectively. The Young's Modulus for the tensile strength test the functionalised carbon nanotubes-polycarbonate copolymer and the functionalised $C_{60}$ fullerene-polycarbonate copolymer of Example 6 were 23.7+/−3.2 and 21.1+/−4.9 MPa respectively.

Example 8: Synthesis of Graphene Oxide Functionalised with Primary Alcoholic Groups Graphene oxide is partially reduced converting the carboxylic acids located on the edge and in the same plane as the graphene sheets into primary alcoholic groups.

5 g of graphene oxide was added to 100 g tetrahydrofuran (THF). 4 g of lithium aluminium hydride was then added and the resulting mixture heated under reflux and sonication for four hours. After cooling, 100 g water was added to precipitate the graphene with primary hydroxyl groups. The mixture was then filtered under vacuum, the functionalised graphene product washed with 500 ml water and then dried under vacuum at 80° C. for 24 hours.

Example 9: Synthesis of Graphene Oxide Functionalised with Primary Amino Groups The carboxylic acids located on the edge in graphene oxide and in the same plane as the graphene sheets are converted in acyl chloride groups. The acyl chloride groups are subsequently converted into amide groups and thence primary amino groups separated from the graphene structure by a single methylene group.

To 5 g of graphene oxide was added 20 g thionyl chloride. The mixture was heated under reflux for two hours after which excess thionyl chloride was removed using a rotary evaporator. A solution of concentrated ammonium hydroxide was then added followed by 100 ml water and stirring continued for three hours. The partially functionalised graphene was filtered out, washed with 200 ml water and dried at 80° C. under vacuum from 24 hours. The partially functionalised graphene was then added to 100 ml THF under sonication at 80° C. 5 g lithium aluminium hydride was then added and the reaction left at 80° C. for 6 hours. Then the reaction mixture was cooled, 100 ml of water added and the graphene with primary amino groups filtered off. The graphene with primary amino groups was then washed with 500 ml water, and dried under vacuum for 24 hours at 80° C.

Example 10: Synthesis of Graphene Oxide Functionalised with Acyl Chloride Groups The carboxylic acids located on the edge in graphene oxide and in the same plane as the graphene sheets are converted in acyl chloride groups.

To 5 g of graphene oxide was added 20 g thionyl chloride. The mixture was heated under reflux for two hours after which excess thionyl chloride was removed using a rotary evaporator. Then the reaction mixture was cooled, 100 ml of water added and the graphene with acyl chloride groups filtered off. The graphene with acyl chloride groups was then washed with 500 ml water, and dried under vacuum for 24 hours at 80° C.

Example 11: Synthesis of Hydrophobically Modified Graphene Oxide Functionalised with Primary Amino Groups Mix 5 g of graphene with acyl chloride groups (see Example 10) and 5 g of 1-dodecanol. Add 40 ml of dry THF and 2 g of triethylamine and stir the mixture for 24 hours at 50° C. Cool the mixture to room temperature and add 20 ml THF. Filter the resulting hydrophobically modified graphene oxide under vacuum, wash with diethyl ether, and then dry overnight under vacuum at 60° C. Treat the hydrophobically modified graphene oxide with concentrated ammonium hydroxide and lithium aluminium hydride as described in Example 9 to convert the remaining acy chloride groups to primary amine groups.

Example 12: Synthesis of Hydrophilically Modified Graphene Oxide Functionalised with Primary Amino Groups Mix 5 g of graphene with acyl chloride groups (see Example 10) and 5 g of triethylene glycol monomethyl ether. Add 40 ml of dry THF and 2 g of triethylamine and stir the mixture for 24 hours at 50° C. Cool the mixture to room temperature and add 20 ml THF. Filter the resulting hydrophobically modified graphene oxide under vacuum, wash with diethyl ether, and then dry overnight under vacuum at 60° C. Treat the hydrophilically modified graphene oxide with concentrated ammonium hydroxide and lithium aluminium hydride as described in Example 9 to convert the remaining acy chloride groups to primary amine groups.

Example 13: Synthesis of Anti-Bacterial Polyamine Modified Graphene Oxide Functionalised with Primary Amino Groups Mix 5 g of graphene with acyl chloride groups (see Example 10) and 5 g of 2-(4-Methyl-piperazin-1-yl)-ethylamine. Add 40 ml of dry THF and 2 g of triethylamine and stir the mixture for 24 hours at 50° C. Cool the mixture to room temperature and add 20 ml THF. Filter the resulting graphene oxide modified by an anti-bacterial polyamine under vacuum, wash with diethyl ether, and then dry overnight under vacuum at 60° C. Treat the hydrophilically modified graphene oxide with concentrated ammonium hydroxide and lithium aluminium hydride as described in Example 9 to convert the remaining acyl chloride groups to primary amine groups.

Example 14: Synthesis of Acrylate Modified Graphene Oxide Functionalised with Primary Hydroxyl Groups Mix 2 g cerium sulphate in the form of a 1% w/w aqueous solution (198 g deionised water purged of oxygen) was added to 5 g of graphene oxide functionalised with primary alcoholic groups prepared according to Example 8 at 50° C. under nitrogen purge. Add 10 g of acrylamide in two 5 g aliquots 20 minutes apart and continue the reaction for three hours.

Then cool, filter, and wash with water. The remaining primary alcoholic groups are free to react with isocyante groups thereby to form composite materials of the invention.

Example 15: Synthesis of Carboxylic Acid Modified Graphene Oxide Functionalised with Primary Hydroxyl Groups Mix 2 g cerium sulphate in the form of a 1% w/w aqueous solution (198 g deionised water purged of oxygen) was added to 5 g of graphene oxide functionalised with primary alcoholic groups prepared according to Example 8 at 50° C. under nitrogen purge. Add 10 g of a 50/50 mixture of acrylamide and acrylic acid in two 5 g aliquots 20 minutes apart and continue the reaction for three hours. Then cool, filter, and wash with water. The remaining primary alcoholic groups are free to react with isocyante groups thereby to form composite materials of the invention.

Example 16: Synthesis of Composite Material According to the Invention Based on any One of the Functionalised Graphene Oxides of Examples 8 to 15

Synthesis of composite material according to the invention based on any one of the functionalised graphene oxides of Examples 8 to 15 can be carried out according to the method described in Example 2.

Example 17: Synthesis of Composite Material According to the Invention Based on any One of the Graphene Oxide Functionalised with Primary Amino Groups of Example 9

A mixture of 55 g of poly(hexamethylene carbonate) diol and 5 g of graphene oxide functionalised with primary amino groups of Example 9 were heated to 80° C. under stirring and nitrogen in order to dissolve the functionalised graphene oxide in the polyol. 16 g 4,4'-methylenebis(phenyl isocyanate) (MDI) was then added and the mixture heated at 80° C., with stirring and under nitrogen for two hours. 23 4 g of dimethylacetamide was then added drop-wise to form a solution of pre-polymer which was then cooled to 40° C.

A solution of 1.8 g ethylenediamine and 0.3 g dibutylamine in 64 g of dimethylacetamide (DMAC) was prepared separately and added drop-wise under vigorous stirring to the pre-polymer solution. After completion of polymerization, 3 g of 1-butanol in 7 g dimethylacetamide was added. The concentration of composite material according to the invention was 20% w/w.

Example 18: Evaluation of Scaffolds for Auricular Reconstruction Based on Composite Material According to Example 17

Auricular reconstruction surgery, following congenital microtia, cancer and trauma, is predominantly performed using sculpted autologous rib cartilage. This is considered to be an unpleasant operation as it can result in donor site morbidity and it is especially difficult for younger patients, who will have to suffer with a permanent scar on their chest. Synthetic scaffold materials offer an alternative solution, with Medpor (porous polyethylene implants from Stryker Corporation) being the current market leader. However, complications associated with extrusion and infection can occur and not many surgeons opt to use the alternative synthetic scaffold material. The ideal scaffold should be made from biocompatible materials, and for auricular reconstruction, should match the biophysical properties of the native cartilage and promote angiogenesis and cellular interactions.

Fabrication of Porous Auricular Scaffold

The 3D scaffolds were fabricated by combining porogen leaching with a solvent casting technique. 150 µm diameter sodium bicarbonate ($NaHCO_3$) salt particles were dispersed in the solution of composite material of Example 17 under ultrasound and degassed under vacuum. The weight ratio of $NaHCO_3$ to composite material was 3:8. The polymer solution was poured onto a flat glass dish (100×100 mm$^2$) and left in an air-circulating oven at 65° C. for three hours until all the solvent evaporated. The polymer was then removed from the glass and submerged in deionised water to dissolve out the $NaHCO_3$ salt particles and form a porous polymeric scaffold.

This procedure was repeated six times until several layers of polymer were built up to produce a thickness of about 10-100 mm. This process resulted in the formation of a porous 3D layer scaffold via DMAC exchange with deionised water and leaching of $NaHCO_3$. The construct was continuously washed with frequent water changes, using pure deionised water, for a period of 36 hours to ensure the complete removal of $NaHCO_3$ and DMAC. The porous sheets of polymer were used in mechanical and biological experiments. In development of human organs, such ear, nose, trachea a porous 3D scaffold encourages growth of blood vessels into it and angiogenesis. This will enhance integration into the surrounding tissue and with stem cells will functionalise physiology to simulate the human organs. At the same time, sheets of polymer with similar thickness, made from solution of composite material of Example 17 were cast without porogen for further testing.

Mechanical Analysis

The previously prepared scaffolds, Medpor® and human auricular cartilage were carefully cut to obtain samples suitable for assessment of their mechanical properties. The tensile strength of the cut samples (n=6) were characterised using an AML tensile tester in accordance with ISO standard 37:2011 (Rubber, vulcanizsed or thermoplastic—Determination of tensile stree-strain properties) as previously described. Briefly, the polymer samples were cut into dumbbell-shaped pieces type 3 (shaft length 20 mm, width 4 mm) using a cutting press (Wallace Instruments, Surrey, UK). Thickness was measured using a digital electronic outside micrometer. Uniaxial tension was applied to either ends of the scaffolds until failure using the AML tester equipped with a 500 N load, pneumatic grips with 1 kN capacity and at a rate of 100 mm/min. System software was used to analyse the polymer's tensile strengths at room temperature.

Stress (MPa) was calculated by dividing the force generated during stretching by the initial cross-sectional area. Strain was calculated as the ratio of the change in length in reference to the original sample length (%). Each sample had an average thickness reading of 6, calculated by an electronic micrometre.

Biocompatibility Evaluation of Scaffolds

The previously prepared scaffolds were cut into 16 mm diameter discs for use in 24 well plates and autoclaved. Medpor® was used for comparison and Tissue Culture Plastic (TCP—polystyrene that has been rendered wettable by oxidation, a treatment that increases its adhesiveness for cells) was used as a control sample.

Human Adipose Stem Cell Cultures

Human adipose tissue-derived stem cells (ADSC) were isolated from fat according to the method described by Naderi et al. (J. Plast. Reconstr. Aesthet. Surg., 67, 12, 1726 (2014)). Adipose tissue was collected from patients undergoing liposuction.

Metabolic Activity—Alamar Blue™ Assay

Medpor® and porous scaffolds prepared from the composite material of the invention (n=6 per group) were placed in 24 well plates and seeded with $2 \times 10^4$ ADSC per scaffold. ADSC cytotoxicity and viability was assessed using the Alamar Blue™ assay (Serotec, Kidlington) on days 1, 3, 7, 14 and 21.

Alamar Blue™ is a commercially available assay which aims to quantitatively assess cell proliferation, cytotoxicity and viability. Changing the colour from dark blue to light pink is the result of reduction due to cell metabolism by viable, metabolically active cells only. This colour change from is measured by monitoring absorbance at 570 nm and 630 nm. The blue dye resazurin has negligible intrinsic fluorescence and absorbance while its reduced product, resorufin, emits a highly fluorescent, pink colour, which can be detected by means of a plate reader equipped with a 570 nm filter. The intensity of fluorescence is proportional to the number of metabolically active cells.

Analysis of Cell Proliferation Using DNA Quantification

To assess ADSC cells proliferation, a Fluorescence Hoechst DNA Quantification Kit (Sigma) was utilized to quantify the DNA content on both the Medpor and the scaffolds prepared from the composite material of the invention on days 1, 3, 7, 14 and 21. Scaffolds (n=6 per group) were seeded with $2 \times 10^4$ ADSCs for analysis.

The total DNA contents of cultured cell were determined using fluorescent Hoechst 33258 stain as previously described by Rago et al. (Anal. Biochem., 191, 31 (1990)). Briefly, cells were lysed (×3) using freeze-thaw cycles following the removal of cell culture supernatants. Lysed cells were stored in a freezer at −80° C. and thawed to room temperature. The lysate were incubated with molecular biology grade water for one hour in each cycle and Hoechst stain (Benzamide 33258, Sigma, UK) was added at a final concentration of 2 µg/ml. The fluorescence of Hoechst dye was measured at 360 nm excitation wavelength and 460 nm emission wavelength using a fluorescence microplate reader (Fluoroskan Ascent FL, Thermo Labsystems, UK). Total DNA and cell number standard curves were obtained from serial dilutions of known DNA concentrations (calf thymus, Sigma, UK) and different cell densities, respectively.

Assessment of Bacteria Resistance of Disc Prepared from the Composite Material of the Invention Filled plates of Muller Hinton agar (Thermo Fisher Scientific Oxoid Ltd) were inoculated with either *Staphylococcus aureus* (strain ATCC 25923) or *Escherichia coli* (strain ATCC 25922) using a sterile cotton swab on the surface of the agar. 16 mm diameter discs of composite material of the invention were placed in the middle of the agar plates (n=6 per group). The plates were incubated for 24 hours at 37° C. in an oxygen control incubator. After the incubation period, the minimal inhibition zone (MIC) was determined around the polymer disc on the agar plate.

Statistical Analysis

The data is presented as means±standard deviations. The statistical significance between the samples was calculated by one-way analysis of variance (ANOVA) at a significance level of less than 0.05 (P<0.05).

Results

Mechanical Analysis

The mechanical properties are shown in Table 1. The maximum tensile strength of the non-porous scaffolds prepared from the composite material of the invention was significantly (P<0.001) higher compared to the porous scaffolds prepared from the composite material of the invention, but only slightly lower than Medpor. However, human auricular cartilage had a maximum tensile strength of only 2.02±0.25 MPa.

TABLE 1

Mechanical properties of cast sheets of prepared from the composite material of the invention (NP) and porous sheets of prepared from the composite material of the invention (P) compared to that of human auricular cartilage and Medpor ® (n = 6).

| Samples | Sample thickness (mm) | Max tensile strength (MPa) | Elongation at break (%) |
|---|---|---|---|
| NP | 0.40 ± 0.01 | 73.10 ± 3.91 | 1030.2 ± 31.1 |
| P | 0.65 ± 0.12 | 4.25 ± 0.23 | 157.2 ± 21.2 |
| Medpor ® | 0.37 ± 0.02 | 6.45 ± 0.26 | 5.0 ± 0.2 |
| Human auricular cartilage | 0.75 ± 0.02 | 2.02 ± 0.25 | 39.0 ± 5.1 |

Biocompatibility Evaluation

Figure 5:
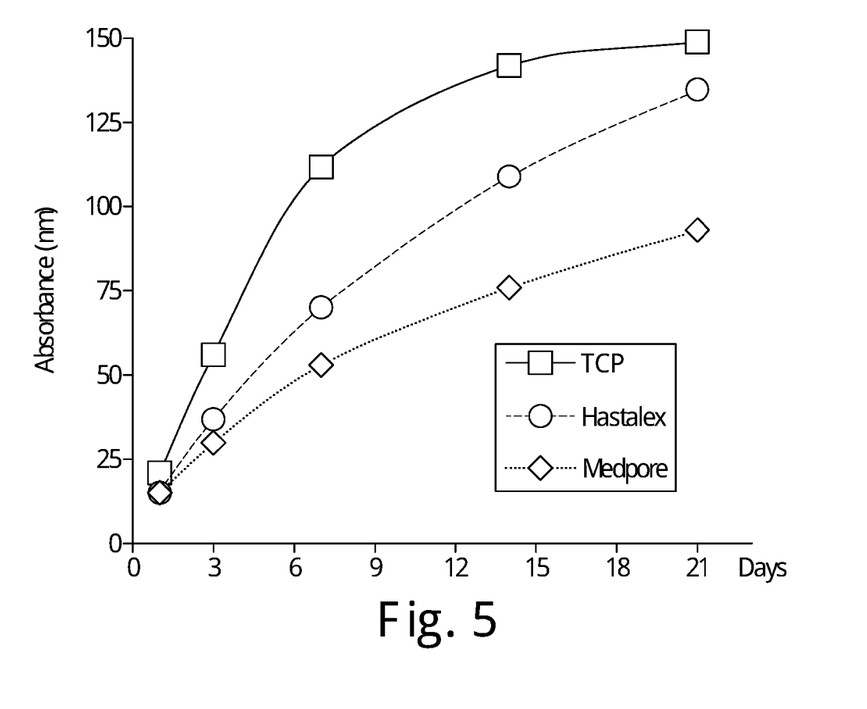
FIG. 5 ADSC cell viability on scaffolds prepared from tissue culture plastic (TCP), porous scaffold prepared from the composite material of Example 17 (Hatalex) and Medpor (porous polyethylene implants from Stryker Corporation) using Alamar blue assay for a period of 21 days.
Figure 6:
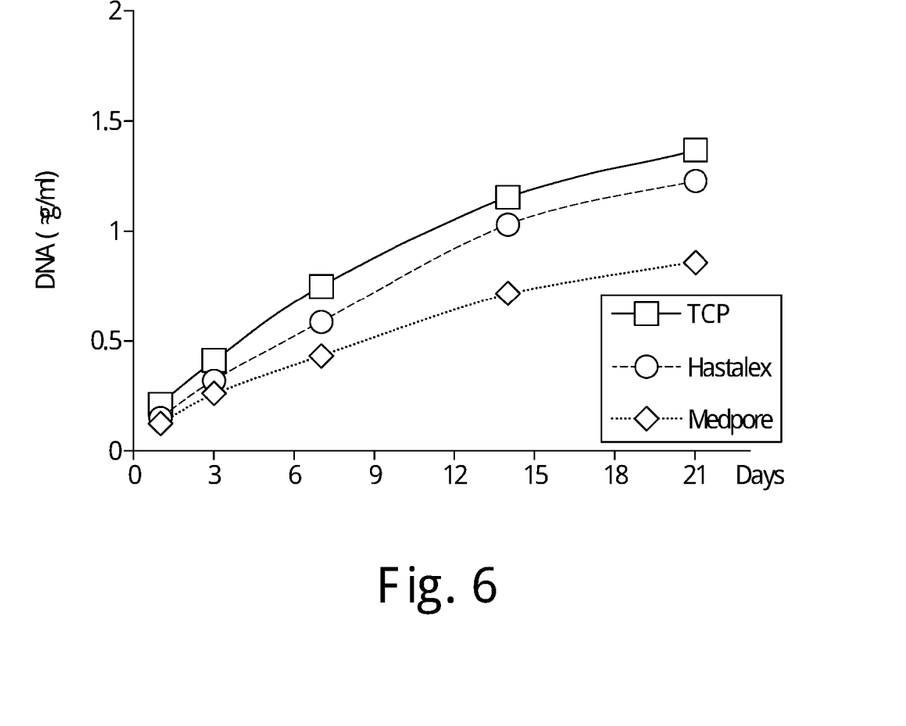
FIG. 6 metabolic activities per total DNA on scaffolds prepared from tissue culture plastic (TCP), porous scaffold prepared from the composite material of Example 17 (Hatalex) and Medpor (porous polyethylene implants from Stryker Corporation) from day 1 to days 21.

The viability of the ADSCs on the porous scaffolds prepared from the composite material of the invention was compared to the viability of the ADSCs on the Medpor and TCP for over 21 days. Both the Alamar Blue™ cell viability assay (FIG. 5) and DNA assay (FIG. 6) demonstrated that more ADSCs were present on the porous scaffolds prepared from the composite material of the invention compared with Medpor at all time-points examined and statistically significance was reported on days 7 (p<0.05), 14 and 21 (p<0.001). The ADSC viability and cell proliferation using DNA assay on the control, TCP, was compared with the porous scaffolds prepared from the composite material of the invention after 21 days of cell culture. FIG. 5 shows no significant statistical difference between cell viability on TCP (tissue culture plastic) compared with porous scaffold prepared from the composite material of the invention after 21 days of cells culture. FIG. 6 shows the metabolic activities per total DNA increase significantly gradually from day 1 to days 21 and that, similarly to the viability readings, the total DNA on day 21 was significantly higher both on TCP and the porous scaffold prepared from the composite material of the invention compared with Medpore (P<0.001) with no significant difference between TCP and the porous scaffold prepared from the composite material of the invention.

Bacteria Resistance Test

Table 2 shows that the disc prepared from the composite material of the invention has bacterial resistance compared with glass.

TABLE 2

The bacterial resistance results of disc prepared from the composite material of the invention and medical grade Pyrex glass control (n=6) after 24 hours of incubation.

| Sample | Staphylococcus aureus | | | | | | Escherichia coli | | | | | |
|---|---|---|---|---|---|---|---|---|---|---|---|---|
| Hastalex | + | + | − | + | + | + | − | + | + | − | ++ | + |
| Glass | − | − | − | − | − | − | − | − | − | − | − | − |

The minimal inhibition zone (MIC), was assigned as "−" indicate for no zone of inhibition, "+" for a clear zone of inhibition <1 mm around the polymer disc, and ++ for a clear zone of inhibition >1 mm around the polymer disc.

Conclusion

This study has shown that the composite material of the invention can be fabricated to a porous 3D scaffold using a salt leaching/casting methodology and result with similar mechanical properties to that of native human auricular cartilage. In addition, it shows that a porous scaffold of the composite material of the invention is biocompatible with ADSC. This study has important implications for auricular and nasal cartilage reconstruction as ADSC is easily available and can be extracted from fat from patients and can be seeded onto the scaffold before implantation under the skin. Furthermore discs prepared from the composite material of the invention have shown bacterial resistance activity compared to glass.

Example 19: Comparative Study of Mechanical Properties of Composite Materials of the Invention Non-porous films were prepared and mechanically tested according to the protocol set forth in Example 18. The results are summarised in Table 3.

TABLE 3

Mechanical properties of casted polymer sheets. Keys: composite materials of the invention in accordance with Example 17 (composite with primary NH$_2$), composite material of the invention in accordance with Example 17 wherein graphene oxide functionalised with primary alcoholic groups is substituted for graphene oxide functionalised with primary amino groups (composite with primary CH$_2$OH), composite material of the invention in accordance with Example 17 wherein graphene oxide is subsituted for graphene oxide functionalised with primary amino groups (GO + PCU) and material of the invention in accordance with Example 17 without graphene oxide functionalised with primary amino groups (PCU). Data are mean ± SD (n = 6).

| Samples | Sample thickness (mm) | Max tensile strength (MPa) | Elongation at break (%) |
|---|---|---|---|
| Composite with primary NH$_2$ | 0.40 ± 0.01 | 79.25 ± 8.54 | 1210 ± 31 |
| Composite with primary CH$_2$OH | 0.40 ± 0.01 | 57.50 ± 5.07 | 920 ± 42 |
| GO + PCU | 0.40 ± 0.02 | 32.00 ± 2.94 | 567 ± 34 |
| PCU | 0.40 ± 0.01 | 24.50 ± 2.65 | 806 ± 11 |

The invention claimed is:

1. A process for producing a composite material comprising a first segment covalently bonded to a second segment by a urethane and optionally a urea and/or an amide linkage, wherein the first segment is a carbon nanoparticle moiety and the second segment is a polyol moiety, the process comprising a first step of polymerising
   (i) a functionalised carbon nanoparticle,
   (ii) a polyol,
   (iii) a compound comprising at least two isocyanate groups, and optionally
   (iv) a chain extending compound comprising at least two chemical groups selected from the group consisting of a primary amine, an hydroxyl and a carboxylic group,
   wherein functionalised means functionalised with any one of carboxylic acid, tertiary alcoholic, epoxide, primary alcoholic or primary amino groups; and
   wherein the process comprises adding (iii) to a solution of (i) in (ii) and polymerising (i), (ii) and (iii).

2. The process according to claim 1, wherein the polyol is selected from the group consisting of a polycarbonate polyol, a polycaprolactone diol, a polyether polyol, a polyester polyol, a polybutadiene polyol, a polyol comprising pendant polyethylene oxide, and mixtures thereof.

3. The process according claim 1, wherein the compound comprising at least two isocyanate groups is an aromatic compound.

4. The process according to claim 1, wherein the compound comprising at least two isocyanate groups comprises two or three or four or five or six isocyanate groups.

5. The process according to claim 1, wherein the compound comprising at least two isocyanate groups is selected from the group consisting of toluene 2,4-diisocyanate, 1,3-bis(1-isocyanato-1-methylethyl)benzene, and methylenebisphenyl isocyanate.

6. The process according to claim 1, wherein the chain extending compound comprising at least two chemical groups, comprises two or three chemical groups.

7. The process according to claim 1, wherein the chain extending compound comprises identical chemical groups.

8. The process according to claim 1, wherein the chain extending compound is selected from the group consisting of an aliphatic amine, an aliphatic carboxylic acid, an aliphatic alcohol, a functionalised silica nanoparticle, an amino acid, a peptide, and a polypeptide.

9. The process according to claim 1, wherein the second segments are of the same polyols.

10. The process according to claim 1, wherein the second segments are of different number average molecular weights.

11. The process according to claim 1, wherein the weight ratio of first segments to second segments is at least 1:50.

12. The process according to claim 1, comprising a second step of adding a monoamine after completion of the first step.

13. The process according to claim 1, wherein the functionalised carbon nanoparticle is selected from the group consisting of functionalised graphene oxide sheets and functionalized graphene sheets, wherein said primary amino groups are present on both the edge and the plane of the sheets.

14. The process according to claim 1, wherein the compound comprising at least two isocyanate groups is an aliphatic compound.

15. The process according to claim 1, wherein the chain extending compound comprises non-identical chemical groups.

16. The process according to claim 1, wherein the second segments are of the same or different polyols.

17. The process according to claim 1, wherein the second segments are of the same or different number average molecular weights.

* * * * *